United States Patent [19]

Brubaker

[11] Patent Number: 4,973,593
[45] Date of Patent: Nov. 27, 1990

[54] NOVEL COMPOUNDS FOR THE TREATMENT OF HYPERTENSION

[75] Inventor: Abram N. Brubaker, Lafayette, Ind.

[73] Assignee: Research Corporation Technologies, Inc., Tucson, Ariz.

[21] Appl. No.: 81,428

[22] Filed: Aug. 4, 1987

[51] Int. Cl.[5] .................. A61K 31/445; C07D 471/10
[52] U.S. Cl. ...................... 514/278; 546/19;
546/20; 546/43; 546/63; 546/15; 548/408;
548/409; 548/147; 548/216; 548/309; 544/6;
544/71; 544/230; 544/231; 514/265; 514/269;
514/226.8; 514/228.8; 514/365; 514/374;
514/385; 514/409
[58] Field of Search ...................... 546/19, 20, 43, 63;
514/278, 265, 269, 226.8, 228.8, 365, 374, 385,
409; 544/230, 6, 71, 230, 231; 548/408, 409,
147, 216, 309

[56] References Cited

PUBLICATIONS

Brubaker et al. "J. Med. Chem" No. 8, vol. 29, pp. 1528–1531 (Aug. 1986).

*Primary Examiner*—Robert T. Bond

*Attorney, Agent, or Firm*—Scully, Scott, Murphy & Presser

[57] ABSTRACT

Compounds of the formulae:

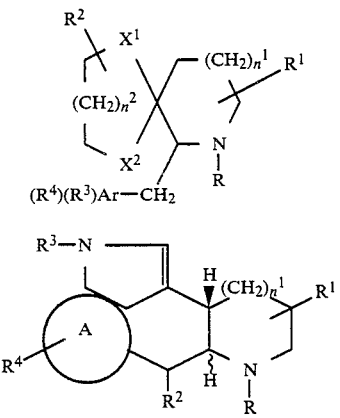

are useful as anti-hypertensives.

26 Claims, No Drawings

NOVEL COMPOUNDS FOR THE TREATMENT OF HYPERTENSION

BACKGROUND OF THE DISCLOSURE

1. Field of the Invention

The present invention relates to novel heterocyclic compounds possessing valuable pharmaceutical activity, particularly dopamine agonist and antihypertensive activities. Novel intermediates, used for preparing the active therapeutic agents, also possess valuable therapeutic properties and are also within the scope of this invention. The present invention is also directed to pharmaceutical compositions containing the novel compounds as well as a method of treating hypertension to a host, including humans by administering to the host an anti-hypertensive effective amount of the compounds of the present invention or salts thereof.

2. Background of the prior art

Azaspirodecanes and azaspirononanes have generally been used as stabilizers. For example:

U.S. Pat. No. 3,959,291 to Cook discloses compounds of the formula:

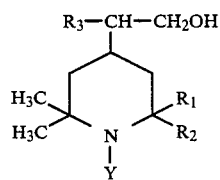

wherein $R_1$ and $R_2$ taken together with the carbon to which they are bound form a cycloalkyl residue having from 5 to 12 carbon atoms in the ring, Y is among other things, an alkyl residue having from 1 to 20 carbon atoms, aralkyl having from to 12 carbon atoms and $R_3$ is hydrogen or a straight or branched chain alkyl residue. These compounds are disclosed as being useful as stabilizers.

Swiss Patentschrift No. 469736 discloses compounds of the formula:

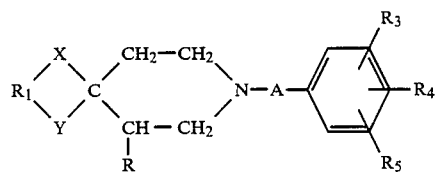

wherein X and Y are independently oxygen or sulfur; $R_1$ is a hydrocarbon chain with 2 to 11 carbon atoms and the total number of carbon atoms in X and Y range from 2-4 carbons; $R_2$ is hydrogen or a methyl group; $R_3$, $R_4$ or $R_5$ are hydrogen, lower alkyl or alkoxy or $R_3$, $R_4$, $R_5$ taken together are 3-4 methylenedioxy and A is alkylene group having up to 5 carbon atoms.

Brunetti, et al. in U.S. Pat. No. 4,105,626 disclose 4-oxopiperidines of the formula:

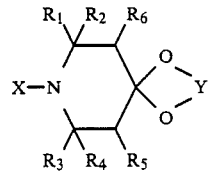

wherein n is 1 or 2, $R_1$ is alkyl having 2 to 6 carbon atoms; $R_2$ is alkyl having 1 to 6 carbon atoms; $R_3$ is alkyl having 1 to 9 carbon atoms, phenyl, benzyl or phenylethyl; $R_4$ is alkyl having 1 to 6 carbon atoms or $R_3$ and $R_4$ taken together with the carbon atom which they are attached form a cyclopentyl or cyclohexyl group; $R_5$ is alkyl having 1 to 5 carbon atoms, alkenyl and alkynyl; $R_6$ is hydrogen, or alkyl having 1 to 5 carbon atoms, alkenyl and alkynyl; X is hydrogen, alkyl having 1 to 8 carbon atoms and Y is $C(R_{11})(R_{12})-CH(R_{13})-$, $-CH(R_{11})-CH_2-C(R_{12})(R_{13})$, $-CH(R_{12})-CH_2-C(R_{11})(R_{13})-$, $-CH_2-C(R_{11})(R_{12})-CH(R_{13})-$, wherein $R_{11}$ is hydrogen, methyl or $CH_2OR_{14}$, $R_{12}$ is hydrogen, methyl or ethyl, $R_{13}$ is hydrogen, methyl or ethyl and $R_{14}$ is hydrogen or an acyl residue. These derivatives are useful as stabilizers for organic polymers against light induced deterioration.

U.S. Pat. No. 4,014,887 to Randell, et al. discloses compositions containing compounds of the formula:

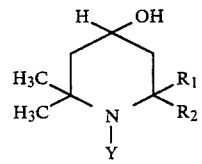

wherein $R_1$ and $R_2$ are the same or different and each is a straight or branched alkyl residue having from 1 to 12 carbon atoms or $R_1$ and $R_2$ together with the carbon to which they are attached form a cycloalkyl group having from 5 to 12 carbon atoms or a piperdine derivative of the formula:

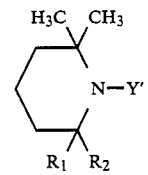

wherein Y' is a straight or branched alkyl residue having from 1 to 20 carbon atoms, an alkenyl group, or alkynyl group having from 7 to 12 carbon atoms, an aralkyl group, etc. It is alleged that the compositions herein possess light stability.

Some researchers have recognized that azaspirodecanes and azaspirononanes have medicinal properties. For example:

Australia Patent No. 248763 discloses compounds of the formula:

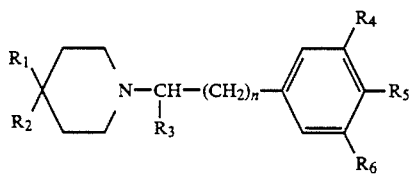

wherein $R_1$ and $R_2$ taken together may form a ring provided by a group selected from $(CH_2)_4$, $(CH_2)_5$ and $(CH_2)_6$; $R_3$ is hydrogen, methyl, ethyl, and propyl, and $R_4$, $R_5$ and $R_6$ are independently hydrogen, alkoxy, hydroxy and its esters and have from 1 to 4 carbon atoms or $R_4$, $R_5$ and $R_6$ may together form a group selected from methylenedioxy and ethylenedioxy and n is an integer from 1 to 3. The compounds therein are disclosed as being useful in the treatment of hypertension.

U.S. Pat. No. 3,282,947 to Grogan discloses unsymmetrically substituted 3,9-diazaspiro(5,5)undecanes of the formula:

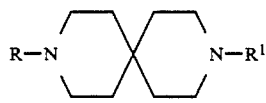

wherein R is among other groups, alkyl, aryl, aroyl, aralkyl, cycloalkyl, heterocyclic alkyl and R' is R or H. The compounds of said formula are alleged to possess useful medicinal utility, and may be useful as local anesthetics, antispasmodics, antihistaminics and hypotensives.

U.S. Pat. No. 3,418,324 to Rice, et al. discloses compounds of the formula:

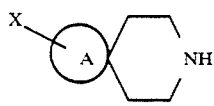

wherein A is selected from the group consisting of monocarbocylic rings having 5 to 15 carbon atoms, hexahydrohydrindenyl and decahydronaphthyl; X is at least one substituent on ring A selected from the group consisting of alkyl of up to 12 carbon atoms, lower alkoxy, lower alkenyl, cycloalkyl of up to 6 carbon atoms, phenyl and naphthyl. Said compounds are disclosed as being intermediates in the preparation of products having medicinal properties.

However, heretofore no attempt has been made to prepare the novel azaspirononanes and azaspirodecanes of the present invention. Furthermore, no one previously has recognized that the spiro compounds of the present invention simultaneously possess anti-hypertensive activity through dopamine receptor stimulation, and unexpectedly lack any central dopamine stimulating activity which is concomitant with most dopamine agonists. Finally, no one recognized heretofore that spiro compounds can be used as important intermediates in the preparation of octahydroindolo [3,4-f,g] quinoline compounds, which also possess dopamine agonist activity, as described hereinbelow.

Compounds based on the ergoline ring system:

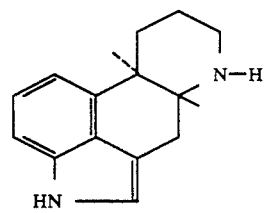

has been shown to have a variety of pharmaceutical activities. For example, the amides of lypergic acid have valuable and unique pharmacological properties and include the naturally occurring peptide alkaloids, ergocornine, ergokryptine, ergonovine, ergocristine, ergosine, and ergotamine synthetic oxytocic alkaloids, such as the synthetic hallucinogenlyseric acid diethylamide or LSD.

Semonsky, et al. in U.S. Pat. No. 3,732,231 disclose D-6-methylergolines of the formula:

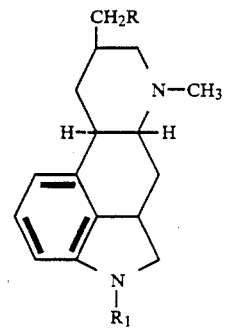

wherein R is chlorine, CN, COOH, COCl, COOCH$_3$, CONHNH$_2$, or CON$_3$ and $R_1$ is hydrogen, where in the case that R is COOH, $R_1$ may be CH$_3$. The reference teaches that the compound D-6-methyl-8-cyanomethylergoline has antifertility activity.

Bernardi, et al. in U.S. Pat. No. 3,228,939 disclose ergoline derivatives of the formula:

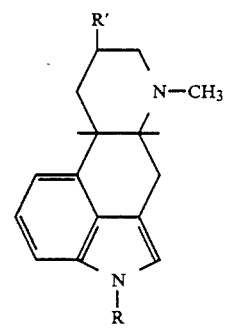

wherein R is hydrogen or nethyl; R' is CONH$_2$ or CH$_2$NHR" and R" is a hydrogen atom or an acylate radical derived from an aliphatic, cycloaliphatic, aromatic or heterocyclic carboxylic acid having 1 to 10 carbon atoms. The compounds are alleged to exhibit oxytocic, antienteraminic, adrenolytic, hypotensive and sedative activity Closely related is U.S. Pat. No. 3,228,942 to Camerino, which discloses 6-methyl and 1,6-dimethyl-8-aminomethylergolines of the formula:

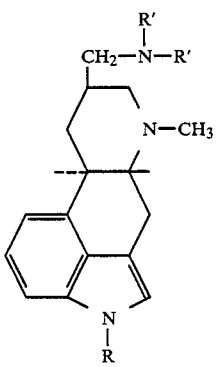

wherein R is hydrogen or methyl, R' is an alkyl, cycloalkyl or aryl radical having from 1 to 9 carbon atoms and R" is a radical of an aliphatic, cycloaliphatic, aromatic or heterocycliccarboxylic acid having from 1 to 10 carbon atoms The compounds herein are alleged to show oxytocic, antienteraminic, adrenolytic, hypotensive and sedative activity.

Arcamone, et al. in U.S. Patent No. 3,646,046 disclose 1,6-dimethyl-10-alpha-ergoline derivatives of the formula:

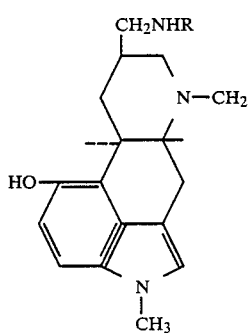

wherein R is selected from the group consisting of the radical of an aliphatic, cycloaliphatic, aromatic and heterocyclic organic acid having from 1 to 10 carbon atoms. Again these compounds are alleged to possess antienteraminic, oxytocic, adrenolytic, hypotensive and sedative activity.

British Patent No. 976065 is directed to 6-methyl and 1,6-dimethyl lumiergoline derivatives of the formula:

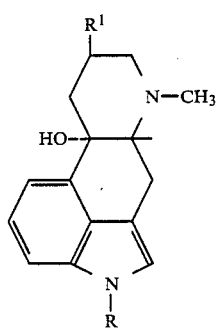

wherein R is hydrogen or methyl and R' is CH$_2$NHR" and R" is hydrogen or a radical of an aliphatic, cycloaliphatic, aromatic or heterocyclic carboxylic or sulfonic acid having from 1 to 10 carbon atoms. The reference teaches that said compounds exhibit oxytocic, antienteraminic, adrenolytic, hypotensive and sedative activities.

U.S. Pat. No. 3,236,852 to Bernardi, et al. disclose esters of 6-methyl and 1,6-dimethyergoline compounds of the formula:

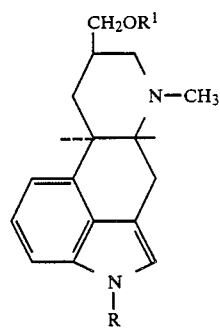

wherein R is hydrogen or methyl and R' is an aliphatic, cycloaliphatic, aromatic or heterocyclic acid having from 3 to 10 carbon atoms. The compounds herein are alleged to exhibit oxytocic, antienteraminic, adrenolytic, hypotenstive and sedative activity.

Hofmann, et al. in U.S. Pat. No. 3,232,942 disclose 1-substituted lysergols of the formula:

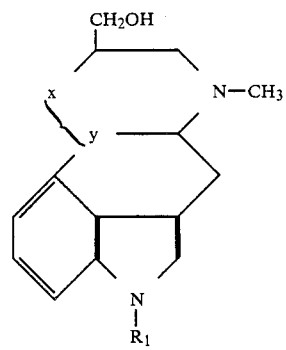

wherein R$_1$ is alkyl containing 1–4 carbon atoms, an aralkyl, alkenyl, and

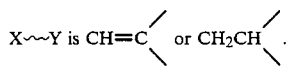

U.S. Pat. No. 3,238,211 to Camerino, et al. discloses alkylamino derivatives of 6-methyl and 1,6-dimethylergolines of the formula:

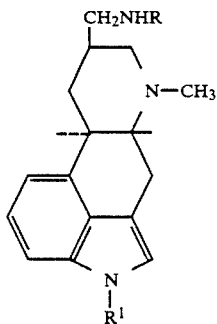

wherein R is hydrogen or a radical of an organic carboxylic or sulfonic acid of the group of aliphatic, cycloaliphatic, aromatic or heterocyclic acids having from 1 to 10 carbon atoms and R' is hydrogen or methyl. Said compounds are alleged to have oxytocic, antienteraminic, adrenolytic, hypotensive and sedative activities.

European Patent Application No. 5646 is directed to tetrahydroindoloisoquinolines of the formula:

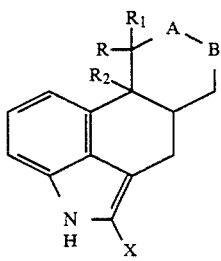

wherein the moiety A–B represents a group of the formula $CH_2NR_3$ or $NR_3CH_2$; $R_3$ represents hydrogen, alkyl, cycloalkyl, cycloalkylalkyl; R represents hydrogen, alkyl or cycloalkyl; $R_1$ and $R_2$ each represent hydrogen or taken together a chemical bond and X is hydrogen or halogen. The compounds herein are alleged to be useful in the treatment of disorders of the central nervous system.

Arcari, et al. in U.S. Pat. No. 3,904,634 disclose bromoergolines of the formula:

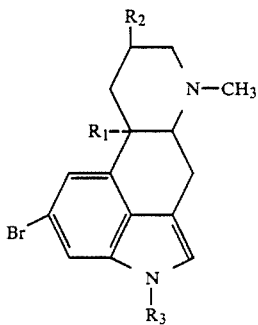

wherein $R_1$ is hydrogen or methoxy, $R_2$ is $CONH_2$ or $CH_2X$; X is $NH_2OH$, or

$R_4$ is aryl or heterocyclic or

and $R_5$ and $R_3$ are hydrogen or methyl. The compounds herein are alleged to exhibit adrenolytic and antienteraminic activity British Patent No. 981827 is directed to lumilysergol derivatives of the formula:

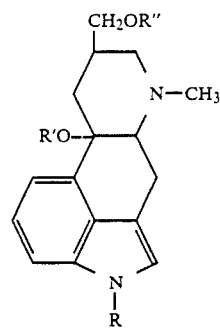

wherein R is hydrogen or methyl, R' is hydrogen or loweralkyl and R'' is hydrogen or a radical of aliphatic, cycloaliphatic, aromatic or heterocyclic carboxylic acids having from 1 to 10 carbon atoms. The compounds herein are alleged to exhibit oxytocic, antienteraminic, adrenolytic, hypotensive and sedative activities.

U.S. Pat. No. 3,879,554 to Temperilli discloses 1,6-dimethyl-8-β-(5-bromonicotinoyloxymethyl)-10α-methoxyergolines of the formula:

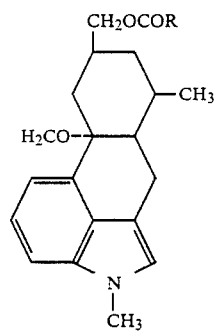

wherein R is methyl or aryl. Said compounds are alleged to be useful in inhibiting blood platelet aggregation and in the treatment of cerebral and peripheral metabolic vascular disorders.

British Patent No. 1,107,156 is directed to ergoline carboxylic acids of the formula:

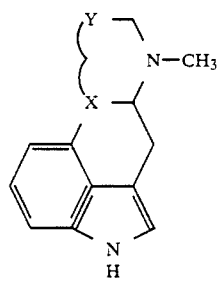

wherein X⁓Y represents the radical of the formula
CH—CH₂—CH, or

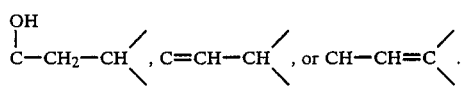

and R represents the radical $(CH_2)_n$—COOH where n is equal to 0 or 1. No utility is disclosed in said patent.

Patentschrift No. 203721 discloses compounds of the formula:

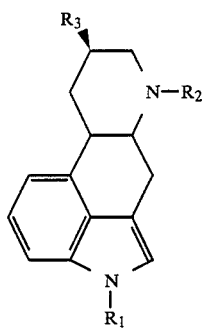

wherein $R_1$ is alkyl, $R_2$ is alkyl and $R_3$, is among other things, hydroxymethyl. The compounds herein are alleged to be vasoconstrictors and to have prolactin-inhibiting properties.

Offenlegungsschrift No. DE3001752 discloses 8-substituted 6-methyl-10-α-H ergolines of the formula:

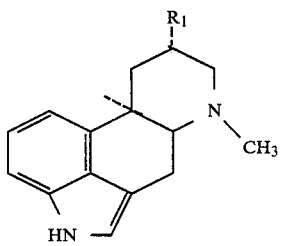

wherein $R_1$ is NH—CO—NR₂, CO—NH—NR₂, CO—NR₂ and CH₂OR₂ and R₂ is hydrogen, methyl or ethyl.

European Patent Application No. 2087889 discloses naphthyridine derivatives of the formula:

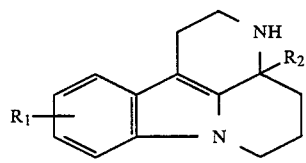

wherein $R_1$ is in the 9 or 10 position and represents hydrogen, halogen or alkyl or alkoxy radical and $R_2$ is a hydrogen or alkyl radical. The compounds herein are alleged to possess antianoxia action and psychotropic action.

U.S. Pat. No. 3,299,078 to Pachter discloses compounds of the formula:

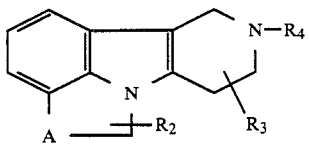

wherein $R_1$ represents hydrogen, halogen, lower alkyl, loweralkoxy or trifluoromethyl; $R_2$ represents hydrogen, loweralkyl or phenyl; $R_3$ represents hydrogen or loweralkyl; $R_4$ represents hydrogen, loweralkyl or benzyl and A represents —CH₂— or —CH₂CH₂—. The compounds herein are alleged to have analgesic, antipyretic, anti-inflammatory, anti-serotonin and central nervous system stimulant activities.

European Patent Application No. 4664 is directed to ester derivatives of lysergol having the formula:

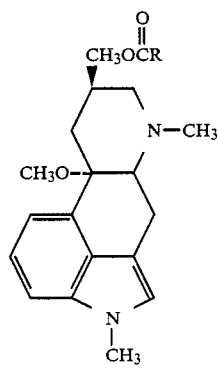

wherein R is an aliphatic, cycloaliphatic, aromatic, heterocyclic radical having up to 10 carbon atoms. The compounds herein are alleged to have adrenolytic and anti-serotonic activity.

Patentschrifft No. 160804 discloses the following compound as a starting material:

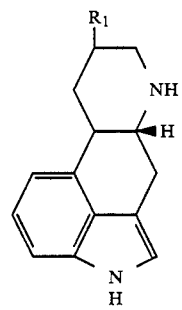

wherein $R_1$ is alkyl, hydroxymethyl, alkoxymethyl, alkoxy carbonyl or a substituted amido group.

Semonsky, et al. in U.S. Patent No. 3,732,231 disclose 8-(beta-aminoethyl)ergolines of the formula:

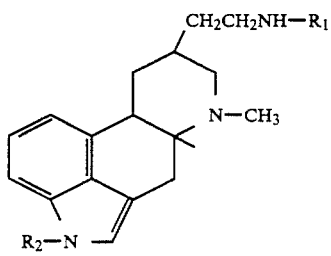

wherein $R_1$ is an hydrogen atom or an acyl group and $R_2$ is hydrogen or methyl. The compounds therein are alleged to have anti-inflammatory and hypotensive activity.

Kornfield, et al. in U.S. Pat. No. 4,246,265 disclose a group of dopaminergic drugs that are allegedly used to treat Parkinsonism and to inhibit prolactin secretion, having the formula:

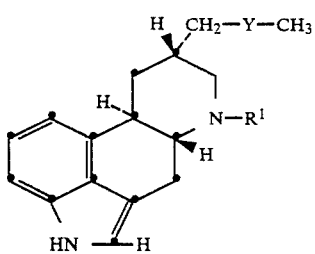

wherein Y is oxygen or sulfur and $R_1$ is n-propyl.

Karepelka discloses, in an article in the *Collection of Czechoslov Chem. Commum,* 42, 1977 pp. 1209–1215, 6-alkylergoline derivatives of the formula:

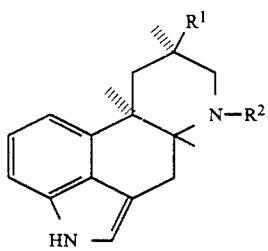

wherein $R_1$ and $R_2$ are methyl; or $R_1$ is methyl and $R_2$ is ethyl, n-propyl, isopropyl, butyl, isobutyl and heptyl; or $R_1$ is methyl and $R_2$ is hydrogen; or $R_1$ is $CH_2OH$ and $R_2$ is ethyl, n-propyl, and n-butyl; or $R_1$ is $CH_2Cl$ and $R_2$ is ethyl, n-propyl and n-butyl. The compounds described herein wherein $R_1$ is methyl exhibit an antilactating and an anti-fertility effects in rats.

Offenlegungsschrift No. DE 3403067 discloses ergoline derivatives of the formula:

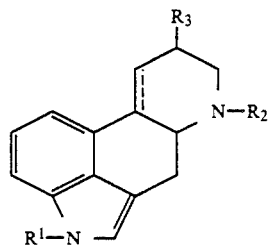

wherein (a) $R_1$ is hydrogen or methyl; $R_2$ is alkyl containing 2 to 8 carbon atoms and can be substituted with 1, 2 or 3 halogen atoms, alkenyl containing 3 to 8 carbon atoms, cycloalkyl, cycloalkylalkyl or alkylcycloalkyl and $R_3$ is methyl, hydroxymethyl, acyloxymethyl, halogenomethyl or methylene or (b) $R_1$ can be alkyl with 2 to 8 carbon atoms which can be substituted with 1, 2 or 3 halogen atoms, alkenyl with 3 to 8 carbon atoms, cycloalkyl with 4 to 7 carbon, cycloalkylalkyl or alkylcycloalkyl; $R_2$ can be a cyclic group, hydrogen, alkyl containing 1, 2 or 3 halogen atoms, alkenyl containing 3 to 8 carbon atoms, cycloalkyl containing 4 to 7 atoms, cycloalkylalkyl or alkylcycloalkyl containing 4 to 7 ring carbon atoms, phenyl or phenylalkyl and $R_3$ is methyl, hydroxymethyl, acyloxymethyl, alkoxymethyl, halogenomethyl or methylene. The compounds disclosed herein can have a double bond in position 8-9 or a double bond in position 9-10 or may have no double bonds at all in either of those positions.

Bach, et al. in U.S. Patent No. Re. 30,218 disclose 8,8,9-6-methyl-ergolines of the formula:

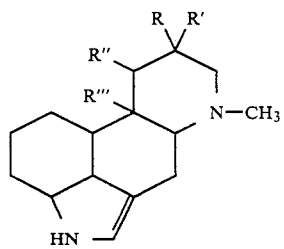

wherein R is alkyl, carbo($C_1$-$C_{13}$) alkoxy, chloro or bromo; R' is carboxyl, carbo ($C_1$-$C_3$) alkoxy or $CH_2Z$ wherein alkyl is (Cl-C3), and Z is H, OH, CN, $OSO_2$ alkyl, Y-phenyl or Y-alkyl wherein Y is S or O and R" and R''' when taken singly are hydrogen and when taken together with the carbon atoms to which they are attached form a double bond. It is alleged that the compounds therein are useful as prolactin inhibitors and/or have activity in the central nervous system.

European Patent Application No. 185392 discloses ergoline compounds of the formula:

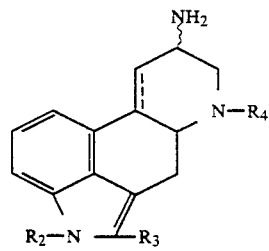

wherein the line between carbon-9 and carbon-10 is a single or double bond, $R_2$ is hydrogen, $C_1$-$C_4$ alkyl or $C_1$-$C_7$-acyl, $R_3$ is hydrogen, chlorine, bromine and $R_4$ is $C_2$-$C_6$ alkyl, $C_3$-$C_6$ cycloalkyl $C_1$-$C_3$ alkyl, $C_3$-$C_6$ alkenyl or $C_2$-$C_6$ alkynyl. The compounds are disclosed to have antidiodopaminergic activity.

European Patent Application No. 43811 discloses indolonaphtyridines of the formula:

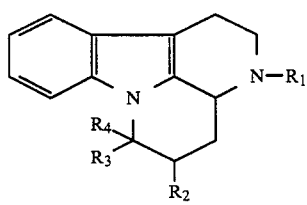

wherein R is hydrogen or alkyl group of 1-6 carbon atoms, $R_4$ is a hydrogen atom, $R_2$ is a hydrogen atom $R_3$ is hydrogen or a hydroxy group and $R_2$ and $R_3$ together form a carbon bond. It is alleged herein that the compounds are active medicaments.

However, heretofore, no attempt has been made to prepare the indoloquinolines of the present invention. Moreover, no one has recognized that the indoloquinolines of the present invention posses potent anti-hypertensive activity through peripheral dopamine receptor stimulation, without any central dopamine stimulating activity.

SUMMARY OF THE INVENTION

The present invention is concerned with novel 7-azaspiro [4,5] nonanes and decanes of Formula I:

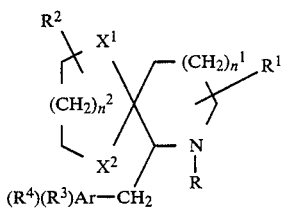

wherein
Ar is aryl, heteroaryl or

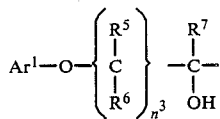

$Ar^1$ is aryl or heteroaryl;
$X^1$ and $X^2$ are independently O, CH, $NR^8$ or S;
R, $R^2$, $R^5$, $R^6$, $R^7$ or $R^8$ are independently hydrogen or lower alkyl or aryl;
$R^1$ is hydrogen lower alkyl, cycloalkyl, hydroxy, lower alkoxy, carboxy, lower carbalkoxy;
$R^3$ and $R^4$ are independently hydrogen, lower alkyl, hydroxy, lower alkoxy amino, lower alkylamino, lower dialkylamino, lower amino alkyl;
$n^1$ is 0 to 1;
$n^2$ is 0, 1, 2 or 3; and
$n^3$ is 1, 2 or 3;
In addition, the present invention relates to the pharmaceutical compositions thereof and the use of the compounds as antihypertensive agents. Compounds of Formula I are intermediate in the formation of the indoloquinolines of Formula II described hereinbelow.

The present invention is also directed to the novel compounds of Formula II:

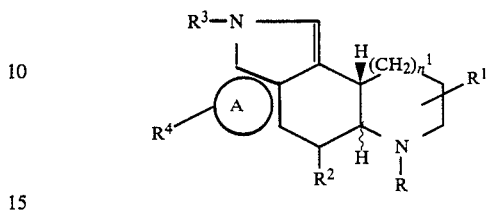

wherein
the A ring is phenyl or naphthyl;
R is hydrogen, lower alkyl, or aryl;
$R^1$ is hydrogen, lower alkyl, lower cycloalkyl, carboxy, lower carbalkoxy, hydroxy or loweralkoxy;
$R^2$ is hydrogen or lower alkyl or aryl;
$R^3$ is hydrogen or lower alkyl;
$R^4$ is hydrogen, lower alkyl, hydroxy, lower alkoxy, amino, lower alkylamino, lower dialkylamino, lower aminoalkyl, or halogen.

These compounds also possess potent anti-hypertensive activity. Therefore, the present invention is also directed to the pharmaceutical compositions thereof and the method of treating hypertension in mammals.

In the formula described hereinabove, the lower alkyl groups, either alone or within the various substituents defined hereinabove, contain up to 6 carbon atoms which may be in the normal or branched configuration, including methyl, ethyl, propyl, isopropyl, butyl, isobutyl, pentyl, isopentyl, hexyl and the like.

The aryl groups are aromatic moieties containing from 6 to 10 ring carbon atoms. This group includes phenyl, α-naphthyl or β-naphthyl. The preferred aryl group is phenyl.

The heteroaryl rings exemplary of Ar and Ar' are 5-10 membered heteroaromatic rings containing at least one oxygen, sulfur or nitrogen. Exemplary heteroaryls include furan, thiophene, pyrrole, imidazole, pyridine, pyrimidine, indole, pyridazine, purine, isoquinoline, quinoline, and the like. The preferred heteroaryl group is indole. The most preferred heterocyclic moiety is 3-indolyl or 4-indolyl. The aryl group and the heteroaryl groups may be unsubstituted or mono- or di-substituted with such groups as hydroxy, alkoxy, alkyl, amino, alkylamino, dialkylamino, aralkyl, aminoalkyl, and the like. It is preferred that these groups may either be unsubstituted or substituted with hydroxy.

The cycloalkyl groups may be mono or polycyclic and contain from 3 to 20 carbons. These groups include cyclopropyl, cyclopentyl, cyclohexyl, cycloheptyl, bornyl, norbornyl and the like. These groups may be partially unsaturated and carry substituents such as halogen, hydroxy, lower alkoxy, lower alkoxy, amino, lower alkylamino, lower aralkyl and the like.

In the formula hereinabove, the ring size is varied through the use of the variables, $n^1$ and $n^2$. For instance, when $n^1$ is 1, then the ring of the compounds of Formula I depicted hereinbelow:

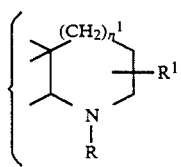

becomes

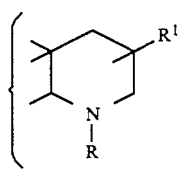

On the other hand, when $n^1$ is 0, then said ring becomes;

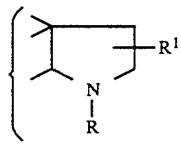

Similarly, when $n^1$ is 1, then the ring of compounds of Formula II depicted hereinbelow:

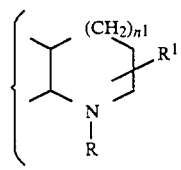

becomes

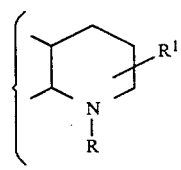

When $n^1$ is 0, then said ring becomes:

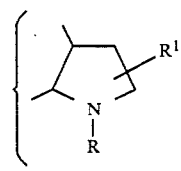

Similarly, when $n^2$ is 0, then the spiro ring of Formula I is a five membered ring, as shown below:

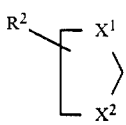

When $n^2$ is 1, then the spiro ring is a six membered ring:

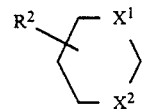

Similarly, when $n^2$ has the values of 2 and 3, the spiro ring is a seven membered or eight membered ring, respectively. The preferred values for $n^2$ is 0 and $n^1$ is 1.

In the formulations of Compounds I described hereinabove, it is to be understood that Ar and $Ar^1$ are substituted by $R^3$ and $R^4$.

With respect to Formula I, the preferred embodiment has the formula:

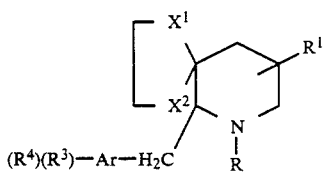

It is preferred that R is lower alkyl, such as methyl, ethyl or propyl. Moreover, the preferred $R^1$ and $R^2$ are hydrogen. It is also preferred that $R^3$ is hydrogen or hydroxy and $R^4$ is hydrogen, hydroxy or lower alkyl. The preferred $X^1$ and $X^2$ groups are both oxygen.

The preferred embodiment of Formula II has the formula:

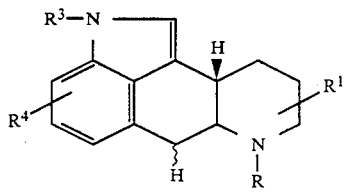

The most preferred value of R is lower alkyl, e.g., methyl, ethyl, n-propyl. The preferred $R^3$ is hydrogen and the preferred value of $R^4$ is hydrogen or hydroxy.

The compounds of the present invention can be prepared by art recognized procedures from known compounds or readily preparable intermediates, as discussed hereinbelow.

An exemplary procedure for the preparation of Compounds of Formula I proceeds through the following intermediate, depicted as Formula IV:

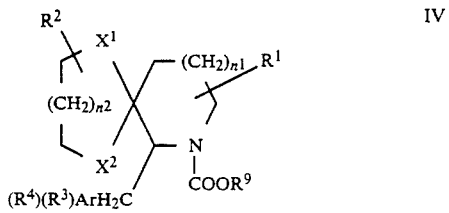

wherein $R^1$, $R^2$, $R^3$, $R^4$, Ar, $X^1$, $X^2$, $n^1$ and $n^2$ have the same meanings as heretofore and $R^9$ is lower alkyl or aralkyl such as benzyl. Basic hydrolysis of IV with strong bases, such as hydroxy, using methods known to one skilled in the art will provide compounds of Formula I wherein R is hydrogen [hereinafter referred to as I¹]. Moreover, reduction of compounds of Formula IV using hydrogenating agents such as hydrogen on palladium or platinum and the like will also produce I¹.

Compounds of Formula I wherein R is methyl can be prepared by using reducing agents, such as lithium aluminum hydride, lithium or titanocene dichloride and the like on compounds of Formula IV by techniques known to one skilled in the art.

Compounds of Formula I wherein R is lower alkyl other than methyl can be prepared by coupling I¹ with a aldehyde of the formula

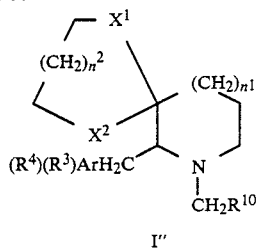

wherein $CH_2R^{10}$ is R and R in the process is defined as alkyl other than methyl. For example:

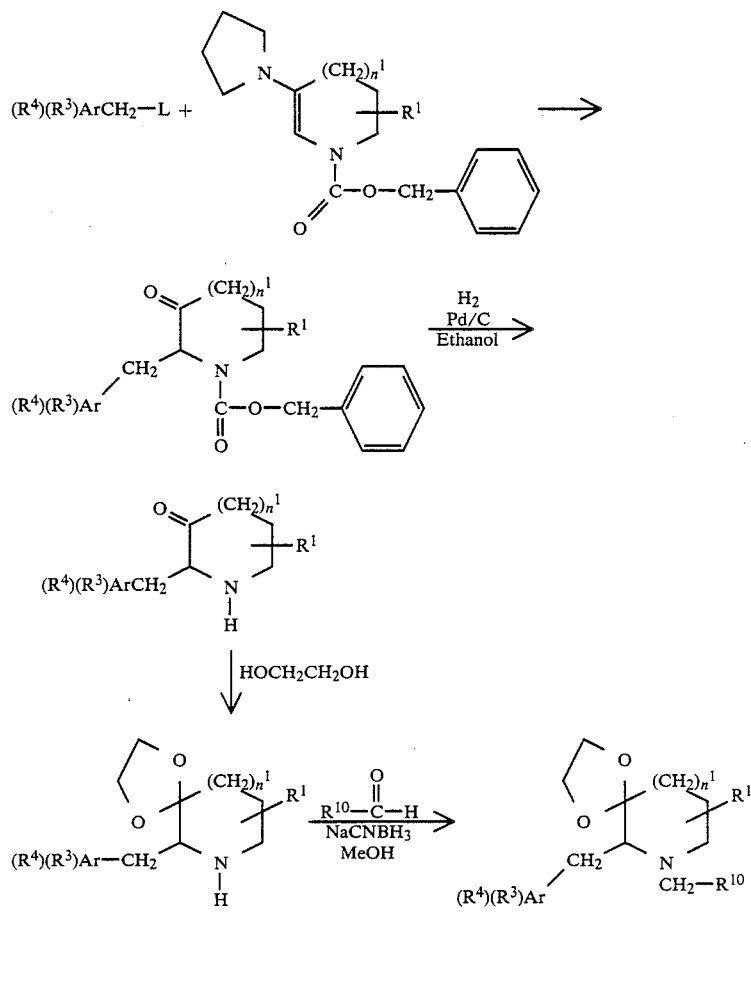

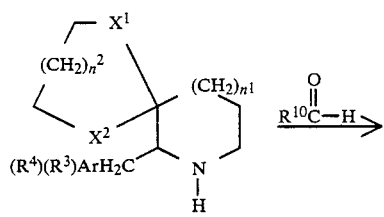

wherein $R^{10}$ is alkyl, under reducing conditions, such as in the presence of sodium cyanoborohydride and the like as shown hereinbelow:

As in any organic reaction, solvents can be employed, such as methylene chloride, diethyl ethers tetrahydrofuran, dioxane, chloroform, and the like. The reaction is normally effected at or near room temperature although temperatures from 0° C. up to the reflux temperatures of the mixture can be employed.

Compounds of Formula IV can be prepared by art-recognized methods in the art.

An exemplary procedure is outlined below:

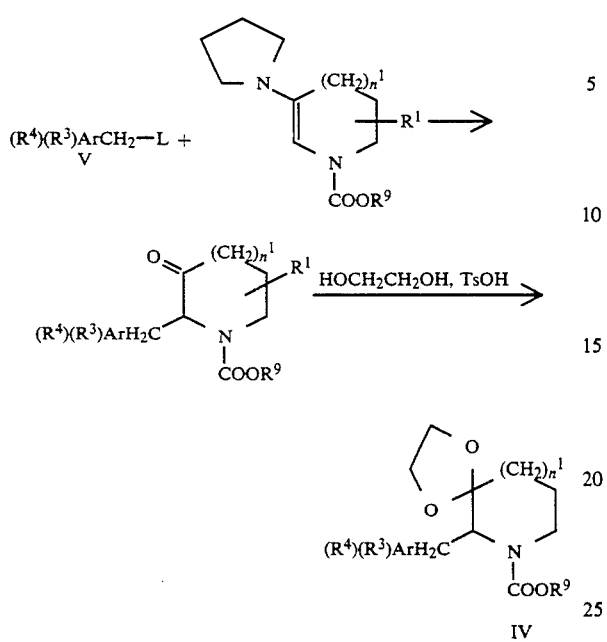

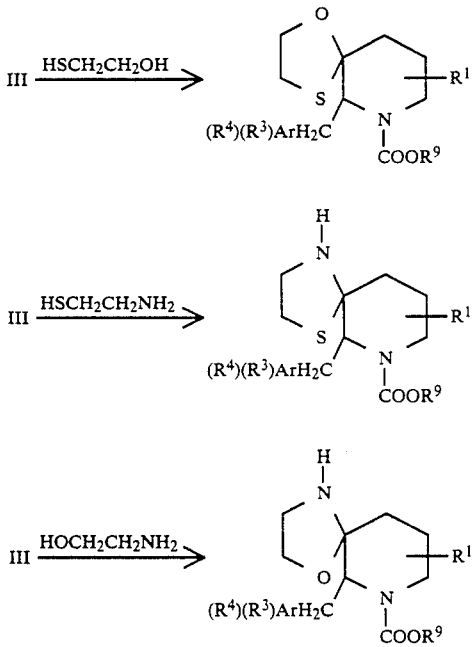

In the above sequence, Ar, $R^1$, $R^2$, $R^3$, $R^9$ and $n^1$ are as defined as heretofore, and L is a good leaving group, such as halide, tosylate, brosylate and the like.

A compound of Formula V is reacted with an enamine of ethyl 3-oxopiperidine-1-carboxylate (VI) according to the method of Krogsgaard-Larsen, et al., in Acta Chem Scand. Ser. B 1976, B 30, 884. The product thereof is reacted with ethylene glycol according to procedures known in the art to form the ketal of Formula IV.

When $X^1$ and $X^2$ are other than oxygen, compounds of Formula IV can be prepared from III as shown below:

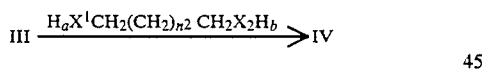

wherein $H_aX^1$ and $H_bX^1$ are independently OH, SH, or $NH_2$.

An exemplary procedure for those compounds wherein $X^1$ and $X^2$ are independently S, O or $NR^8$ is depicted below:

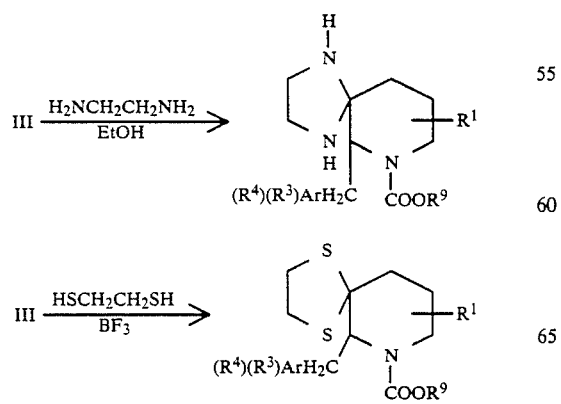

When either $X^1$ and $X^2$ are carbon, then the following scheme is exemplary for the preparation of compounds of Formula IV from Formula III:

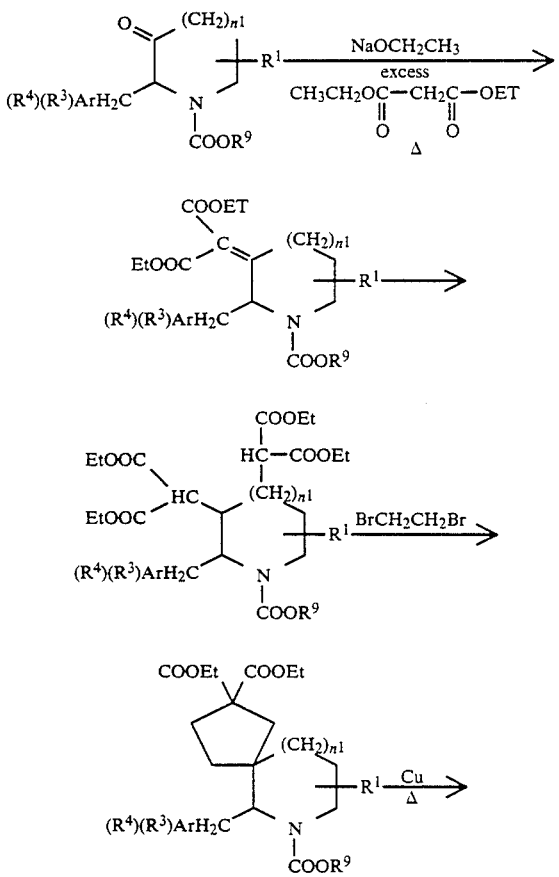

The indoloquinolines can be prepared from the spiro compounds formulated hereinabove by techniques known to one skilled in the art. An exemplary procedure is depicted hereinbelow in Scheme I; wherein $R^9$ is described hereinabove.

SCHEME I

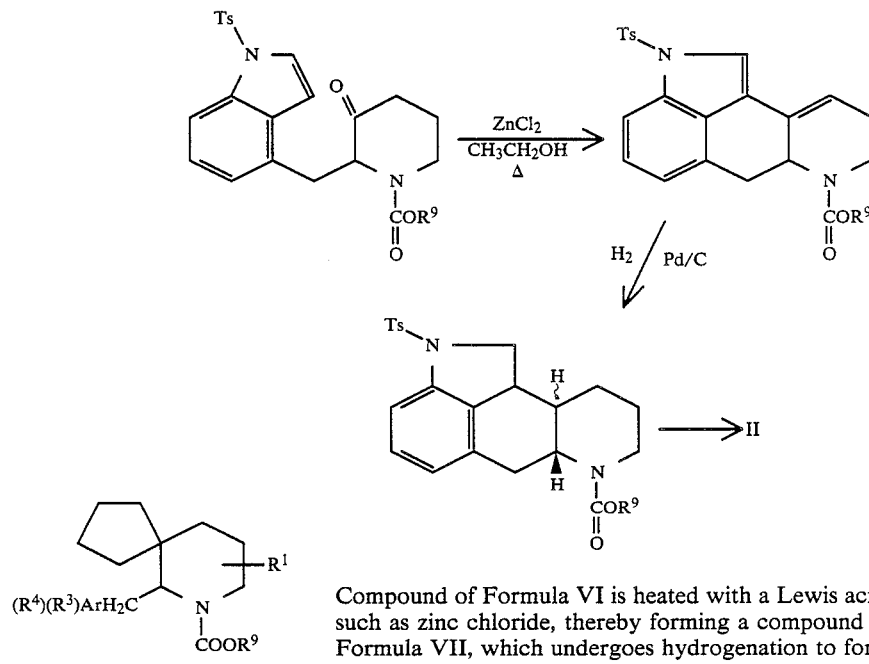

Condensation of a compound of Formula III with a diester in the presence of a strong base under Claisen or Stobbe condensation conditions followed by dinucleophilic attack by a compound of Formula L-$(CH_2)_n$-L and dicarboxylation will lead to a product of Formula IV.

Compound of Formula VI is heated with a Lewis acid, such as zinc chloride, thereby forming a compound of Formula VII, which undergoes hydrogenation to form a compound of Formula VIII.

If $R^9$ is benzyl or alkyl, then the following scheme is also applicable:

SCHEME II

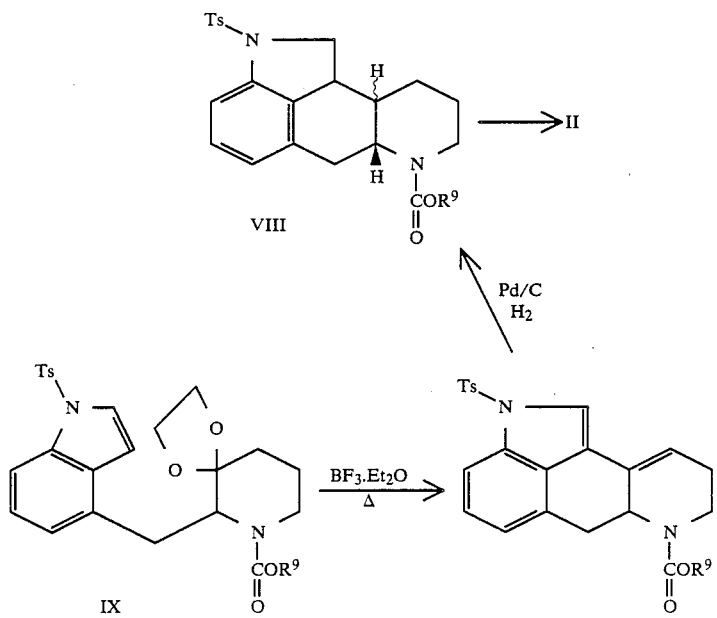

A compound of Formula IX is reacted with a Lewis acid, such as borontrifluride to provide a compound of Formula X.

The compounds of Formula VIII can be converted to compounds of Formula II, according to the procedure described earlier in the present specification.

Various substituents on the present new compound, as defined in Ar, can be present in the starting compounds, added to any one of the intermediates or added after formation of the hydroxamate products by the known methods of substitution or conversion reactions. If the substituents themselves are reactive, then the substituents can themselves be protected according to the techniques known in the art. A variety of protecting groups known in the art may be employed. Examples of many of these possible groups may be found in "Protective Groups in Organic Synthesis" by T. W. Green, John Wiley and Sons, 1981. For example, the nitro groups can be added to the aromatic ring by nitration and the nitro group converted to other groups, such as amino by reduction, and halo and hydroxy by diazotization of the amino group and replacement of the diazo group. Alkanoyl groups can be substituted onto the aryl groups by Friedel-Crafts acylation. The acyl groups can then be transformed to the corresponding alkyl groups by various methods, including the Wolff-Kishner reduction and Clemmenson reduction. Amino groups can be alkylated to form mono and dialkylamino groups; and hydroxy groups can be alkylated to form corresponding ethers. Thus, substitution or alteration reactions can be employed to provide a variety of substituents throughout the molecule of the starting material, intermediates, or the final product.

The present compounds form salts with acids when a basic amino function is present and salts with bases when an acid function, i.e., carboxy, is present. All such salts are useful in the isolation and/or purification of the new products. Of particular value are the pharmaceutically acceptable salts with both acids and bases. Suitable acids include, for example, hydrochloric, sulfuric, nitric, benzenesulfonic, toluenesulfonic, acetic, malic, tartaric and the like which are pharmaceutically acceptable. Basic salts for pharmaceutical use are the Na, K, Ca and Mg salts.

The compounds of the present invention can be administered to the host in a variety of forms adapted to the chosen route of administration, i.e., orally, intravenously, intramuscularly or subcutaneous, topically or inhalation routes.

The active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 0.1 to about 10% of the weight of the unit. The amount of active compound in such therapeutically useful compositions is such that a suitable dosage will be obtained. Preferred compositions or preparations according to the present invention are prepared so that an oral dosage unit form contains between about 0.1 and 100 mg of active compound.

The tablets, troches, pills, capsules and the like may also contain the following: A binder such as gum, tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

The following examples further illustrate the invention:

EXAMPLE 1

6-(4-Indolylmethyl)-7-methyl-1,4-dioxa-7-azaspiro[4.5]-decane (11)

A. Ethyl 3-Oxopiperidine-1-carboxylate (6). To a stirred and cooled (ice bath) solution of 1-benzyl-3-piperidone hydrochloride hydrate (51 g, 0.226 mol), Et$_3$N (35 mL, 0.25 mol), and CHCl$_3$ (250 mL) was added dropwise ClCO$_2$CH$_2$CH$_3$ (24 mL 27 g, 0.25 mol). After addition was complete, additional ClCO$_2$CH$_2$CH$_3$(15 mL) was added to the flask, and the reaction was then stirred at 25° C. for 1 hour. The CHCl$_3$ solution was washed with 1N HCl, and the volatiles were evaporated to give 6 as an orange oil, which was distilled to yield 28 g (72%) of 6 after a forerun of benzyl chloride: bp 105° C. (1 mm) NMR: δ 1.27 (t, 3H), 1.97 (m, 2H), 3.92 (s, 2H, and 4.08 (q, 2H); IR (film) 1700, 1725 (sh) cm$^{-1}$.

B. Ethyl 2-[[4-(p-Tolylsulfonyl)indolyl]methyl]-3-oxopiperidine-1-carboxylate (9). A solution of 6 (3.6 g, 21 mmol), pyrrolidine (2.24 g, 31.5 mmol), and C$_6$H$_6$ (100 mL) was stirred at 25° C. for 1 hour. Analysis by vapor-phase chromatography revealed that the reaction was almost complete, and then the flask was heated and 50 mL of C$_6$H$_6$ was distilled and collected in a Dean-Stark trap. A solution of 4-(bromoethyl)-1-(p-tolylsulfonyl)indole (8) in CH$_3$CN (100 mL) was added to the flask in one portion, and an additional 50 mL of solvent was distilled from the flask with continued hearing. TLC analysis of the reaction mixture after the second distillation of solvent revealed that no starting material remained, and after cooling, the volatiles were evaporated. The dark oil that remained was stirred with 5% NaHCO$_3$ at 80° C. for 30 minutes; then it was cooled, and the product was extracted from the aqueous layer with EtOAc. The organic layers were combined and dried (Na$_2$SO$_4$), and the volatiles were evaporated to give a dark oil, which was chromatographed to yield 6.69 g (77%) of 9 that would not crystallize: $^1$H NMR (CCl$_4$) δ 0.5–4.2 (unresolved br m, 16H), 4.62 (t, 1H), and 6.5–7.9 (m, 9H); IR (film) 1720 (sh), 1705 cm$^{-1}$.

C. Ethyl 6-[[4-(p-Tolylsulfonyl)indolyl]methyl]-1,4-dioxa-7-azaspiro[4.5]decame-7-carboxylate (10). A mixture of 9 (6.6 g, 14.5 mmol), HOCH$_2$CH$_2$OH (6 mL), TsOH H$_2$O (0.1 g), and C$_6$H$_6$ (150 mL) was heated to reflux, and the water that formed was removed with a Dean-Stark trap. After 12 hours, the reaction was allowed to cool, and the solution was washed successively with 5% NaHCO$_3$ and saturated NaCl and dried (Na$_2$SO$_4$). Evaporation of the volatiles gave an oil that solidified, and the solid was recrystallized from EtOAc to yield 5.5 g (77%) of 10 as thick needles: mp 152°–155° C.; $^1$H NMR (CCl$_4$)δ0.2–4.4 (unresolved br m, 21H), and 6.67-7.87 (m, 9H); IR (KBr) 1680 cm$^{-1}$. Anal. (C$_{26}$H$_{30}$N$_2$O$_6$S)C, H, N.

D. 6-(4-Indolylmethyl-7-methyl-1,4-dioxa-7-azaspiro[4.5]decane (11). A mixture of 10 (4.23 g, 8.5 mmol), LiAlH$_4$ (0.975 g, 25.7 mmol), and THF (50 mL) was heated at reflux, 12 hours, and after cool (ice bath), saturated Na$_2$SO$_4$ was added dropwise cautiously to the mixture with stirring until the suspended solid became white. The solution was filtered, and the filter cake was washed with several portions of hot THF. The volatiles of the combined filtrates were evaporated to give an oil, which soon solidified. The solid was recrystallized from EtOAc to yield 1.86 g (76%) of colorless cubes: mp 181°–186° C.: $^1$H NMR (CDCl$_3$/(CD$_3$)$_2$SO)δ1.5–1.9 (br m, 4H), 2.2–2.3 (m and s, 4H), 2.75 (m, 1H), 3.0–3.2 (m, 3H), 4.0 (s, 4H), 6.6–7.2 (m, 5H) and 7.63 (br s, 1H, exchanges with D$_2$O. Anal. (C$_{17}$H$_{22}$N$_2$O$_2$)C, H, N.

EXAMPLE 2

6-(3-Indolylmethyl)-7-methyl-1,4-dioxa-7-azaspiro[4.5]-decane (15)

A. Ethyl 6-(3-Indolylmethyl)-1,4-dioxa-7-azaspiro[4.5]decane-7-carboxylate (14). A mixture of 6 (1.71 g, 10 mmol), pyrrolidine (1.2 mL, 1.02 g, 14.4 mmol), and C$_6$H$_6$ was stirred for 30 minutes at 25° C.; then the mixture was heated to reflux and 15 mL of solvent was collected in a Dean-Stark trap. After the flask had cooled, the volatiles were evaporated, and then 3-(pyrrolidin-1-ylmethyl)indole (2.0 g, 10 mmol) in CH$_3$CN (25 mL) was added to the flask, and this mixture was heated to reflux. After 48 h, additional 6 (1.0 g) was added to the flask and refluxed for 24 hours. The mixture was cooled and 1N HCl (25 mL) was added to the flask, and this mixture was then stirred for 1 hour at 25° C. The product was extracted from the aqueous layer with EtOAc, and the combined organic layers were washed with 5% NaHCO$_3$ and saturated NaCl and dried (Na$_2$SO$_4$). Evaporation of the volatiles gave a red oil that resisted all attempts to crystallize it. This oil was used in the next step without further purification. A solution of crude 13, HOCH$_2$CH$_2$OH (3.0 g, 50 mmol), and TsOH H$_2$O (0.03 g) was warmed (80° C.) on the rotary evaporator until H$_2$O ceased to distill from the flask. Purification of the crude oil by chromatography gave an oil that crystallized from Et-OAc/C$_6$H$_{12}$ to yield 3.25 g (94%) of 14 as off-white clusters: mp 122°–125° C.; $^1$H NMR (CDCl$_3$) δ 0.4–1.1 (2 m, 3H), 1.8 (m, 4H), 2.8–3.2(m, 3H), 3.2–4.8(m and br s, 8H), 6.8–7.6 (m, 5H), and 8.3 (br s, 1H); IR (KBr) 3300, 2950, 1675 cm$^{-1}$ Anal. (C$_{19}$H$_{24}$N$_2$O$_4$) C, H, N.

B. 6-(3-Indolylmethyl)-7-methyl-1,4-dioxa-7-azaspiro[4.5]-decane (15). A solution of 14 (2.5 g, 7.3 mmol) in THF (20 mL) was added dropwise to a stirred suspension of LiAlH$_4$ (0.55 g, 14.5 mmol) in THF (25 mL). After addition was complete, the mixture was heated at reflux for 24 hours. The reaction was cooled, and H$_2$O (0.55 mL), 15% NaOH (0.55 mL), and H$_2$O (1.65 mL) were added sequentially. The mixture was filtered, and the filtrate was evaporated to give an oil that solidified. Recrystallization of the solid from EtOAc yielded 0.7 g (34%) of 15 as cubes: mp 207° C.; $^1$H NMR (CDCl$_3$/CD$_3$)$_2$SO) δ 1.3–1.9 (m, 4H), 2.2 (s and m, 4 H), 2.6–3.2 (m, 4H), 3.9 (s, 4H), and 6.8–7.6 (m, 5H). Anal. (C$_{17}$H$_{22}$N$_2$O$_2$) C, H, N.

EXAMPLE 3

6-Benzyl-7-methyl-1,4-dioxa-7-azaspiro[4.5]decane (18)

A. Ethyl 2-Benzyl-3-oxopiperidine-1-carboxylate (16). A solution of pyrrolidine (1.0 g, 1.2 mL, 15 mmol), 6 (1.71 g, 10 mmol), and C6H6 (25 mL) was stirred at 25° C. for 30 minutes. The solution was then heated to reflux and solvent was collected in a Dean-Stark trap until no more H2O was formed. The remaining volatiles were evaporated, and benzyl chloride (1.26 g, 11 mmol) in CH3CN (25 mL) was added to the crude enamine 7, and this mixture was stirred at reflux for 48 hours. After the mixture cooled, 1N HCl (50 mL) was added to the flask, and the product was extracted from the aqueous layer with Et2O. The Et2O layers were combined and evaporated, and the red oil that remained was distilled to yield 1.3 g (50%) of 16 as a light yellow oil: bp 155°-160° C (0.3 mm); $^1$H NMR (CC14) δ 0.9-1.4 (2 t, 3H), 2.4-2.6 (m and t, 4 H), 2.9-3.2 (d and m, 3H), 3.6-4.2 (m, 3H), 4.6 (t, 1H), and 7.08 (br s, 5H); IR (film) 1720 (sh), 1700 cm$^{-1}$. Anal. (C14H19NO3) C, H, N.

B. Ethyl 6-Benzyl-1,4-dioxa-7-azaspiro[4.5]decane-7-carboxylate (17). A solution of 16 (1.4 g, 5.4 mmol), HO(CH2)2OH (1.05 g, 17 mmol), and TsOH H2O was warmed (80° C.) with stirring. After 5 minutes, C6H6 was added to the flask and the solution was heated to reflux. When water that formed during the reaction ceased to collect in the Dean-Stark trap, the solution was allowed to cool and was washed successively with 1N HCl, 5% NaHCO3 and saturated NaCl. The volatiles were evaporated, and the oil that remained was combined with the crude oil from a previous reaction. The crude product was distilled to yield 1.7 g (89%) of 17 as a clear liquid: bp 150°-155° C. (0.3 mm); $^1$H NMR (CDCl3) 0.8-1.2 (m, 3H), 1.6-2.0 (m, 4H), 2.8-3.1 (m, 3H), 3.6-4.6 (m, 8H), and 7.2 (s, 5H); IR (film) 2960, 2900, 1700 cm$^{-1}$. Anal. (C17H23NO4) C, H, N.

C. 6-Benzyl-7-methyl-1,4-dioxa-7-azaspiro[4.5]decane (18). A solution of 17 (1.7 g, 5.6 mmol) in THF (10 mL) was added dropwise to a stirred suspension of LiAlH4 (0.5 g, 13 mmol) in THF (5 mL). After addition was complete, the mixture was heated at reflux for 12 hours; then H2O (0.5 mL), 15% NaOH (0.5 mL), and H2O (1.5 mL) were added successively to the cooled flask. The solution was filtered, and the volatiles were evaporated to give an oil, which was distilled to yield 1 g (72%) of 18 as a yellow liquid: bp 120°-125° C. (0.3 mm);

$^1$H NMR (CDCl3) δ 1.5.1.9 (m, 4H), 2.2-2.4 (m and s, 4H), 2.6-2.9 (m, 4H), 3.9 (s, 4H), and 7.2 (s, 5H). Anal. (C15H21NO2) C, H, N.

Similarly, by using the appropriate starting materials and reagents, the following compounds are prepared:
6-[4-hydroxyphenylmethyl]-7-methyl-1,4-dioxa-7-azaspiro[4.5]decane.
6-[3-hydroxyphenylmethyl]-7-methyl-1,4-dioxa-7-azaspiro[4.5]decane.
6-[3,4-dihydroxyphenylmethyl]-7-methyl-1,4-dioxa-7-azaspiro[4.5]decane.

EXAMPLE 4

A. Ethyl 2-[[4-(p-Tolylsulfonyl)indolyl]methyl]-3-oxopiperidine-1-carboxylate (9) is heated with borontrifluoride in ether. The resulting product is hydrogenerated with hydrogen on palladium in ethanol. The resulting product is then reduced with lithium aluminum hydride in THF to give the desired compound:

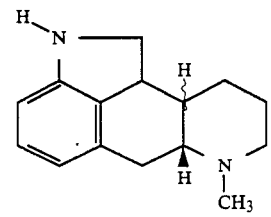

B. Similarly, the following compound can be prepared by the following method:

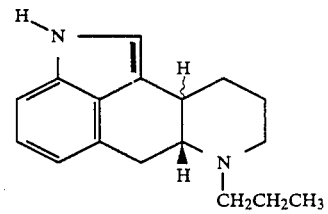

9 is heated with borontrifluoride in ether. The resulting product is hydrogenated with hydrogen on palladium in ethanol. The resulting product is then reacted with acetaldehyde in MeOH following by reduction with sodium cyanoborohydride to produce the desired product.

EXAMPLE 5

Tablets each containing 10 mg of active ingredient are made up as follows:

| | |
|---|---|
| Active ingredient | 10 mg |
| Potato Starch | 45 mg |
| Lactose | 35 mg |
| Polyvinylpyrrolidone (as 10% solution in water) | 4 mg |
| Sodium starch glycolate | 4.5 mg |
| Magnesium Stearate | 0.5 mg |
| Talc | 1 mg |
| Total | 100 mg |

The active ingredient, starch and lactose are passed through a No. 44 mesh B.S. sieve and mixed thoroughly. The solution of polyvinylpyrrolidone is mixed with the resultant powders which are then passed through a No. 12 mesh B.S. sieve. The granules so produced are dried at 50°-60° C. and is passed through No. 16 mesh B.S. sieve. The sodium starch glycolate, magnesium stearate and talc, previously passed through a No. 60 mesh B.S. sieve, are then added to the granules which, after mixing, are compressed on a tablet machine to yield tablets each weighing 100 mg.

EXAMPLE 6

Capsules each containing 20 mg of medicament are made as follows:

| | |
|---|---|
| Active ingredient | 20 mg |
| Starch | 89 mg |
| Lactose | 89 mg |
| Magnesium Stearate | 2 mg |
| Total | 200 mg |

The active ingredient, lactose, starch and magnesium stearate are passed through a No. 44 mesh B.S. sieve and filled into hard gelatin capsules in 200 mg quantities.

EXAMPLE 7

Suppositories each containing 25 mg of active ingredient are made as follows:

| Medicament | 25 mg |
|---|---|
| Saturated fatty acid glycerides to | 2,000 mg |

The active ingredient is passed through a No. 60 mesh B.S. sieve and suspended in the saturated fatty acid glycerides previously melted using the minimum heat necessary. The mixture is then poured into a suppository mould of nominal 2 g capacity and allowed to cool.

EXAMPLE 8

Suspensions each containing 5 mg of medicament per ml dose are made as follows:

| Medicament | 5 mg |
|---|---|
| Sodium carboxymethylcellulose 50 | 50 mg |
| Syrup | 1.25 ml |
| Benzoic Acid solution | 0.01 ml |
| Flavour | q.s. |
| Color | q.s. |
| Chloroform water to | 5 ml |

The medicament is passed through a No. 44 mesh B.S. sieve and mixed with the sodium carboxymethylcellulose 50 and syrup to form a smooth paste. The benzoic acid solution, flavour and color are diluted with some of the chloroform water and added, with constant stirring. Sufficient chloroform water is then added to produce the required volume.

The compounds of the present invention possess peripheral dopamine agonist activity. Unlike other dopamine agonists, the compounds of the present invention are devoid of any central dopamine stimulating activity, which is extremely beneficial in the treatment of high blood pressure. These compounds of Formula I and II are effective on only visceral and systemic dopamine receptors. Unlike other dopamine agonists, the compounds of the present invention are inactive at dopamine receptors in the brain, and therefore lack the central nervous system side effects, such as drug induced psychosis, ataxia, and vomitting, which is exhibited by other dopamine agonists.

Moreover, the compounds of the present invention are potent hypotensive agents and are effective in lowering the blood pressure. It is the combination of the selectivity (as described in the previous paragraph) together with the potency which makes the compounds of the present invention desirable hypotensive agents.

The effectiveness of the compounds of the present invention are shown by the experiments below:

Pharmacology Methods.

A. Cat Cardioaccelerator Nerve Assay.

Cats were anesthetized by injection of pentobarbital sodium (30 mg/kg) into the thoracic cavity, and the surgical and experimental procedure was according to the procedure described in Cannon, J. G., et al. in J. Med. Chem. 1984, 27, 186. Experimental compounds were administered intravenously in doses of 0.33 log intervals.

B. Rotation Assay.

Male Sprague-Dawley rats with 6-hydroxydopamine unilateral denervation of the nigrostriatal projection were used to test compounds for circling behavior according to the procedure of Cannon, et al. in J. Med. Chem 1984, 27, 186. Compounds were administered at a dose of 4.0 mg/kg and were also evaluated for their ability to antagonize apomorphine (0.25 mg/kg) induced rotations.

C. Dopamine Receptor Binding Studies.

A method of Seeman, et al., Proc. Natl. Acad. Sci. U.S.A., 1975, 72, 4376, was employed using [$^3$H]spiroperidol (2 nM) and rat striatal tissue.

The data for these experiments is depicted in Table I:

TABLE I

Biological Potencies of 6-Substituted 7-Methyl-1,4-dioxa-7-azaspiro[4.5]decanes

| compd | dose, mol/kg, iv[a] | % inhibn of nerve stimulation | cat cardioaccelerator nerve: ID$_{50}$, mol/kg |
|---|---|---|---|
| 11 | 0.035 | 26 ± 19 | 0.095[b] (0.001–1.55)[c] |
|  | 0.105 | 48 ± 21 |  |
|  | 0.315 | 79 ± 11 |  |
| 15 | 3.5 | 32 ± 17.4[d,e] | >4.0 |
| 18 | 0.46 | 22 ± 11.7 | >4.0 |
|  | 1.38 | 18 ± 2.0[e] |  |
|  | 4.60 | 36 ± 12.3[d] |  |

[a]N=3 for each concentration tested. [b]Inhibitory effect was reversed by intravenous administration of haloperidol, 50 g/kg. [c]Confidence limits (95%) of the calculated ID$_{50}$ dose. [d]Increased arterial pressure at this dose. [e]Increased heart rate slightly at this dose.

The compounds 11, 15, and 18 were evaluated for in vivo dopamine agonist activity in the cat cardioaccelerator nerve assay. This assay measures the effectiveness of the compounds for peripheral dopamine agonist activity as shown by the data in Table I, these compounds have effective agonist activity.

Compound 11 was also evaluated for its ability to displace [$^3$H] spiroperidol (2nm) from rat striatal tissue. It was inactive in this assay. In other words, it does not bond to dopamine receptor in the CNS.

Finally, the compounds 11, 15, and 18 were evaluated for in vivo rat rotation assay. None of the compounds screened produced rotational behavior in rats with unilateral lesions of the nigrostriatal projection at a dose of 4.0 mg/kg, nor did they antagonize apomorphine-induced rotations in rats in the same assay.

What is claimed is:

1. A compound of the formula:

$$\begin{array}{c} R^2 \\ X^1 \\ (CH_2)_{n^2} \\ X^2 \\ (R^4)(R^3)Ar-CH_2 \end{array} \begin{array}{c} (CH_2)_{n^1} R^1 \\ N \\ | \\ R \end{array}$$

wherein:
Ar is aryl, heteroaryl or

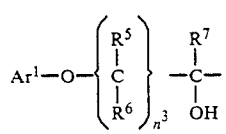

Ar¹ is aryl or heteroaryl;

X¹ and X² are independently O, CH, NR⁸ or S;

R, R², R⁵, R⁶, R⁷, and R⁸ are independently hydrogen, lower alkyl or aryl;

R¹ is hydrogen, lower alkyl, cycloalkyl, hydroxy, lower alkoxy, carboxy, lowercarbalkoxy;

R³ and R⁶ are independently hydrogen, lower alkyl, hydroxy, lower alkoxy, amino, lower alkylamino, diloweralkyl amino, or lower amino alkyl;

n¹ is 0 or 1;

n² is 0, 1, 2, or 3; and n³ is 1, 2, or 3; wherein aryl is an aromatic group containing from 6 to 10 ring carbon atoms; heteroaryl is an heteroaromatic selected from the group consisting of purine, furan, thiophene, pyrrole, imidazole, pyridine, pyrmidine, indole, pyridazine, isoquinoline an quinoline, and cycloalkyl contains from 3 to 20 carbon atoms.

2. The compound according to claim 1 wherein X¹ and X² are both O.

3. The compound according to claim 1 wherein Ar is indolyl or phenyl.

4. The compound according to claim 3 wherein indolyl is 3- or 4-indolyl.

5. The compound according to claim 1 wherein n¹ is 1.

6. The compound according to claim 1 wherein n² is 0.

7. The compound according to claim 1 wherein R³ is hydroxy or hydrogen and R⁴ is hydrogen, hydroxy, or lower alkyl.

8. The compound according to claim 1 wherein R¹ and R² are both hydrogen.

9. The compound according to claim 1 where R is methyl, ethyl, or n-propyl.

10. The compound according to claim 1 wherein Ar¹ is phenyl, R⁴, R⁵ and R⁶ are hydrogen and n³ is 1.

11. A compound of the formula:

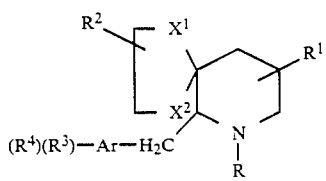

wherein

Ar¹ is aryl, heteroaryl or

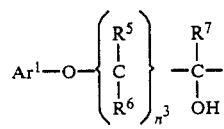

Ar¹ is aryl or heteroaryl;

X¹ and X¹ are independently O, CH, NR⁸, or S;

R, R², R⁵, R⁶, R⁷, R⁸ are independently hydrogen or lower alkyl or aryl;

R¹ is hydrogen, lower alkyl, cycloalkyl, hydroxy, lower alkoxy, carboxy, lower carbalkoxy;

R³ and R⁶ are independently hydrogen, lower alkyl, hydroxy, lower alkoxy, amino, lower alkylamino, diloweralkylamino, or lower aminoalkyl; and n³ is 1, 2, or 3;

wherein aryl is an aromatic group containing from 6 to 10 ring carbon atoms; heteroaryl is an heteroaromatic selected from the group consisting of purine, furan, thiophene, pyrrole, imidazole, pyridine, pyrmidine, indole, pyridazine, isoquinoline and quinoline, and cycloalkyl contains from 3 to 20 carbon atoms.

12. The compound according to claim 11 wherein X¹ and X² are both O.

13. The compound according to claim 11 wherein Ar is indolyl or phenyl.

14. The compound according to claim 13 wherein indolyl is 3- or 4-indolyl.

15. The compound according to claim 11 wherein R³ is hydroxy or hydrogen and R⁴ is hydrogen, hydroxy or lower alkyl.

16. The compound according to claim 11 wherein R¹ and R² are both hydrogen.

17. The compound according to claim 11 wherein R is methyl, ethyl, or n-propyl.

18. The compound according to claim 11 wherein Ar¹ is phenyl, R⁴, R⁵, and R⁶ are hydrogen and n³ is 1.

19. The compound according to claim 1 which is 6-(4-indolylmethyl)-7-methyl-1,4-dioxa-7-azaspiro[4.5]decane.

20. The compound according to claim 1 which is 6-(3-indolylmethyl)-7-methyl-1,4-dioxa-7-azaspiro[4.5]decane.

21. The compound according to claim 1 which is 6-Benzyl-7-methyl-1,4-dioxa-7-azaspiro[4.5]decane.

22. A pharmaceutical composition comprising an effective amount of a compound according to claim 1 and a pharmaceutical carrier therefor.

23. A method of treating hypertension in mammals, which comprises administering to said mammal an antihypertensive effective amount of a compound according to claim 1 or a pharmaceutically acceptable salt thereof.

24. The compound according to claim 1 which is 6-[4-hydroxyphenylmethyl]-7-methyl-1,4-dioxa-7-azaspiro[4.5]decane.

25. The compound according to claim 1 which is 6-[3-hydroxyphenylmethyl]-7-methyl-1,4-dioxa-7-azaspirodecane.

26. The compound according to claim 1 which is 6-[3,4-dihydroxyphenylmethyl]-7-methyl-1,4-dioxa-7-azaspirodecane.

* * * * *

UNITED STATES PATENT AND TRADEMARK OFFICE
CERTIFICATE OF CORRECTION

PATENT NO. : 4,973,593

DATED : November 27, 1990

INVENTOR(S) : Abram N. Brubaker

It is certified that error appears in the above-identified patent and that said Letters Patent is hereby corrected as shown below:

Column 1, line 42: "from to 12" should read as --from 7 to 12--

Column 5, line 21: "atoms The" should read as --atoms. The--

Column 13, line 64: "0 to 1" should read as --0 or 1--

Column 26, line 51: "$cm^{-1}$ Anal." should read as --$cm^{-1}$. Anal.--

Column 26, line 65: "SO) $\xi$ 1.3" should read as --SO): $\xi$ 1.3--

Column 27, line 18: "$(CC_{14})$" should read as --$(CCl_4)$--

Column 32, lines 60 & 61, Claim 25: "azaspirodecane." should read as --azaspiro[4.5]decane.--

Column 32, line 64, Claim 26: "azaspirodecane." should read as --azaspiro[4.5]decane.--

Signed and Sealed this

Twenty-first Day of July, 1992

*Attest:*

DOUGLAS B. COMER

*Attesting Officer*     *Acting Commissioner of Patents and Trademarks*